(12) United States Patent
Mash et al.

(10) Patent No.: US 6,348,456 B1
(45) Date of Patent: Feb. 19, 2002

(54) METHOD OF TREATING CHEMICAL DEPENDENCY IN MAMMALS AND A COMPOSITION THEREFOR

(76) Inventors: Deborah C. Mash; Juan Sanchez-Ramos, both of 1501 NW. 9th Ave., Miami, FL (US) 33136; W. Lee Hearn, 1 Bob Hope Rd., Miami, FL (US) 33136-1133

( * ) Notice: Subject to any disclaimer, the term of this patent is extended or adjusted under 35 U.S.C. 154(b) by 191 days.

(21) Appl. No.: 08/727,123

(22) Filed: Oct. 8, 1996

Related U.S. Application Data

(63) Continuation of application No. 08/280,187, filed on Jul. 25, 1994, now abandoned.

(51) Int. Cl.[7] .................. A01N 43/46; A61K 31/55; C07D 487/00; C07D 491/00
(52) U.S. Cl. .................. 514/214; 514/216; 540/520; 540/521
(58) Field of Search ................ 540/520, 521; 514/214, 216

(56) References Cited

U.S. PATENT DOCUMENTS 5,591,738 A * 1/1997 Lotsof ................ 514/214

\* cited by examiner

*Primary Examiner*—Mukund J. Shah
*Assistant Examiner*—Tamthom N. Truong
(74) *Attorney, Agent, or Firm*—Malin, Haley & DiMaggio, P.A.

(57) ABSTRACT

An essentially pure noribogaine compound having the formula:

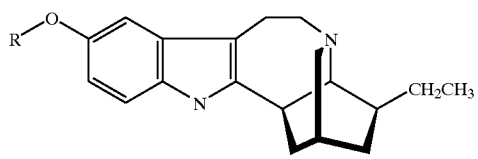

wherein R is hydrogen or a hydrolyzable group of the formula:

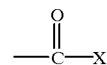

wherein X is an unsubstituted $C_1$–$C_{12}$ group or a $C_1$–$C_{12}$ group substituted by lower alkyl or lower alkoxy groups, wherein the noribogaine compound having the hydrolyzable group hydrolyzes in vivo to form 12-hydroxy ibogamine.

18 Claims, 1 Drawing Sheet

METHOD OF TREATING CHEMICAL DEPENDENCY IN MAMMALS AND A COMPOSITION THEREFOR

This application is a continuation of U.S. patent application Ser. No. 08/280,187, filed Jul. 25, 1994, entitled "A Method Of Treating Chemical Dependency In Mammals And A Composition Therefor", now abandoned.

BACKGROUND OF THE INVENTION

1. Field of the Invention

The present invention provides a method of treating chemical dependency in mammals and a composition therefore.

2. Discussion of the Background

Ibogaine is one of at least 12 alkaloids found in the *Tabernanthe iboga* shrub of West Africa. The indigenous peoples have used the drug in ritual, ordeal or initiation portions in large dosages and as a stimulant in smaller doses. One of the earliest European references to the drug was made by Professor Baillon on the Mar. 6th, 1889 session of the Linnaen Society in Paris during which he described samples obtained by Griffon de Bellay from Gabon and the French Congo.

Early isolation, and identification of ibogaine was accomplished by Dybowski and Landrin (Compt. rend. ac. sc. 133:748, 1901); Haller and Heckel (ibid. 133:850); Lambert and Heckel (ibid. 133:1236) and Landrin (Bull. sc. pharm. 11:1905).

There was little interest in the drug until Raymond-Hamet and his associates Rothlin, E. and Raymon-Hamet published the "Effect of Ibogaine on the Isolated Rabbit Uterus" in 1938 (Compt. rend. soc. biol. 127:592–4). Raymond-Hamet continued to study the drug for a period of 22 years, and singularly published 9 papers: Pharmacological Action of Ibogaine (Arch. intern. pharmacodynamie, 63:27–39, 1939), Two physiological Properties Common to Ibogaine And Cocaine (Compt. rend. soc. biol. 133:426–9, 1940), Ibogaine And Ephedrine (Ibid. 134:541–4, 1940), Difference Between Physiological Action of Ibogaine And That of Cocaine (Ibid. 211:285–8, 1940), Mediate And Intermediate Effects Of Ibogaine On The Intestine (Compt. rend. soc. biol. 135 176–79, 1941), Pharmacologic Antagonism Of Ibogaine (Compt. rend. 212:768–771, 1941), Some Color Reactions Of Ibogaine (Bull. soc. chim. Biol., 25:205–10, 1943), Sympathicosthenic Action Of Ibogaine On The Vessels Of the Dog's Paw (Compt. rend 223:757–58, 1946), and Interpretation Of The Ultraviolet Absoption Curves Of Ibogaine And Tabernanthine (Ibid. 229:1359–61, 1949).

Vincent, conducted work on ibogaine in collaboration with Sero, Inhibiting Action Of Tabernanthe Iboga On Serum Cholinesterase (Compt. rend. Soc. Biol. 136:612–14, 1942). Vincent published five other papers: The Ultraviolet Absorption Spectrum Of Ibogaine (Brustier, B., Vincent D., & Sero, I., (Compt. rend., 216:909–11, 1943), Detection of Cholinesterase Inhibiting Alkaloids (Vincent, D. & Beaujard, P., Ann. pharm. franc. 3:22–26, 1945), The Cholinesterase Of The Pancreas: Its Behavior In the Presence Of Some Inhibitors In Comparison With The Cholinesterases of Serum And Brain (Vincent, D. & Lagreu, P., Bull. soc. chim. biol. 31:1043–45, 1949); and two papers, which he and Raymond-Hamet co-authored: Action Of Some Sympathicosthenic Alkaloids On the Cholinesterases (Compt. rend. soc. biol., 150:1384–1386, 1956) and On Some Pharmacological Effects Of Three Alkaloids Of Tabernanthe Iboga, Bailion: Ibogaine, Iboluteine And Tabernanthine (Compt. rend. soc. biol., 154:2223–2227, 1960).

The structure of ibogaine was investigated by Dickel et al. (J. A. C. S. 80, 123, 1958). The first total synthesis was cited by Buchi et al. (J. A. C. S., 87, 2073, 1965) and (J. A. C. S. 88, 3099, 1966).

In 1956 Salmoiraghi and Page elucidated the relation between ibogaine and serotonin (J. Pharm & expt. ther. 120 (1), 20–25, 1957.9). Contemporaneously, Schneider published three papers. The first, Potentiation Action Of Ibogaine On Morphine Analgesia was done in collaboration with Marie McArthur (Experiential 12:323–324, 1956), while the second was Neuropharmacological Studies of Ibogaine: An Indole Alkaloid With Central-Stimulant Properties (Schneider, J. A. & Sigg, E. B., Annals of N.Y. Acad, of Sciences, Vol. 66:765–776, 1957). The third was An Analysis Of the Cardiovascular Action Of Ibogaine HCL (Schneider, J. A. & Rinehard, R. K., Arch. int. pharmacodyn., 110:92–102, 1957).

The stimulant properties of ibogaine were further investigated by Chen and Bohner, (J. Pharm. & Expt. Ther., 123 (3): 212–215, 1958). Gerson and Lang published A Psychological Study Of Some Indole Alkaloids (Arch. intern. pharmacodynamie, 135:31–56, 1962).

In 1963, Bunag evaluated certain aspects of the relationship between ibogaine and Substance P (Bugag, R. D.; Walaszek, E. J. The Cardiovascular Effects of Substance P in the Chicken Ann. N.Y. Acad. Sci. 104, Part 1, 437–48, 1963).

In 1969, Naranjo reported on the effects of both ibogaine and harmine on human subjects in his paper: Psychotherapeutic Possibilities Of New Fantasy-Enhancing Drug (Clinical Toxicology, 2 (2): 209–224, June 1969).

As a doctoral thesis in 1971, Dhahir published A Comparative Study of The Toxicity Of Ibogaine And Serotonin (University Microfilm International 71-25-341, Ann Arbor, Mich.). This thesis provides an overview of much of the work accomplished with ibogaine.

Additionally, studies of interest also include: The Effects Of Some Hallucinogens On Aggressiveness Of Mice And Rats (Kostowski et al., Pharmacology 7:259–263, 1972), Cerebral Pharmacokinetics Of Tremor-Producing Harmala And Iboga Alkaloids (Zetler et al., Pharmacology 7 (40: 237–248, 1972), High Affinity 3H-Serotonin Binding To Caudate: Inhibition By Hallucinogenic And Serotonergic Drugs (Whitaker, P. & Seeman, P., Psychopharmacology 59:1–5, 1978, Biochemistry), Selective Labeling Of Serotonin Receptors by d-(3H) Lysergic Acid Diethylamide In Calf Caudate (Proc. natl. acad. sci., USA, Vol. 75, No. 12, 5783–5787, Dec. 1978, Biochemistry) and A Common Mechanism Of Lysergic Acid, Indolealkylamine And Phenthylamine Hallucinogens: Serotonergic mediation of Behavioral Effects In Rats (Sloviter, Robert et al., J. Pharm. Expt. Ther., 214 (2):231–238, 1980).

Ibogaine is an alkaloid of the formula:

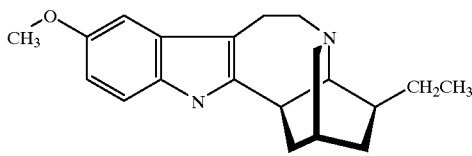

Ibogaine

It is an intriguing structure, which combines the structural features of tryptamine, tetrahydrohavaine and indoloazepines. The total synthesis of ibogaine has been reported. See Buchi, G. et al, *J. Am. Chem. Soc.,* 1966, 88, 2099 (1966); Rosenmund, P. et al, *Chem. Ber.,* 108, 1871 (1975) and Huffman et al, *J. Org. Chem.,* 50, 1460 (1985).

More recently, it was discovered that ibogaine was effective as an "interrupter" of withdrawal and dependence for a variety of agents, such as heroin, cocaine, alcohol, amphetamine, caffeine and nicotine, for example. See U.S. Pat. Nos. 4,587,234, 4,857,523, 4,499,096, 5,026,697 and 5,152,994. Despite a certain and potent effect, however, studies have failed to elucidate a mechanism of action. For example, studies of the binding properties of ibogaine to a large number of neurotransmitter receptor clones has failed to detect any significant pharmacology activities that would explain its mechanism of action.

Nevertheless, administration of ibogaine has proven to be generally effective in mammals for treating chemical dependency. Such dependencies include those to substances which are as diverse as heroin, cocaine, alcohol and nicotine.

However, the effects of ibogaine are relatively short in duration and are generally not observed beyond 24 hours after administration. Thus, a need exists for an agent which is as effective as ibogaine in treating chemical dependencies, yet which is longer lasting in effect.

SUMMARY OF THE INVENTION

Accordingly, it is an object of the present invention to provide an agent which, when administered to mammals, can reduce craving for addictive substances therein.

It is, moreover, an object of the present invention to provide an agent for treating chemical dependency in mammals which is longer acting than ibogaine on the mammalian host.

It is also an object of the present invention to provide a pharmaceutical composition for reducing craving for additive substances in mammals.

Further, it is also an object of the present invention to provide a method of treating chemical dependency in a mammal, which entails administering to a mammal in need thereof an amount of essentially noribogaine or a hydrolyzable derivative thereof.

These advantages and others are provided by an essentially pure noribogaine compound having the formula:

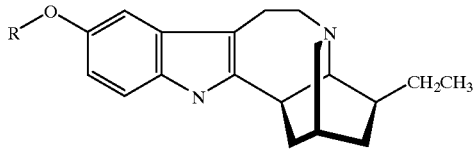

wherein R is hydrogen or a hydrolyzable group of the formula:

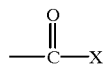

wherein X is an unsubstituted $C_1$–$C_{12}$ group or a $C_1$–$C_{12}$ group substituted by lower alkyl or lower alkoxy groups, wherein the noribogaine having the hydrolyzable group hydrolyzes in vivo to form 12-hydroxy ibogamine.

DETAILED DESCRIPTION OF THE PREFERRED EMBODIMENTS

Figure 1:
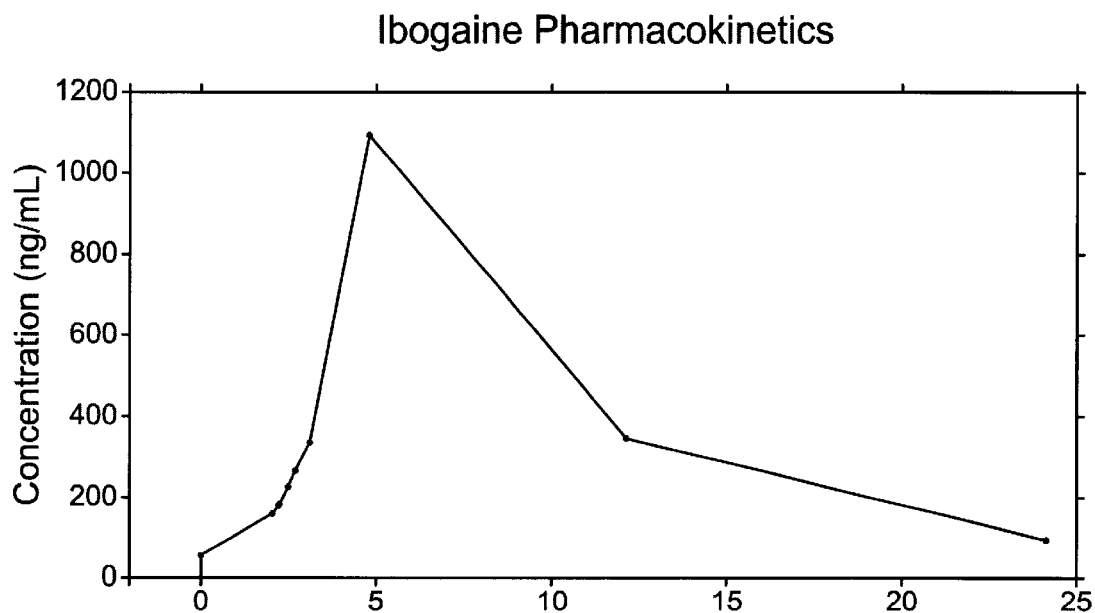
FIG. 1 is a graphical plot of ibogaine pharmacokinetics in a human as a function of blood concentration versus time.

The present invention is predicated upon the surprising discovery of a new class of noribogaine compounds which have a greater and longer lasting activity in mammals than ibogaine for reducing craving for addictive substances, and treating chemical dependency.

In accordance with the present invention, it has been surprisingly discovered that noribogaine, a metabolite of ibogaine, and certain hydrolyzable esters of noribogaine have a much longer lasting effect than ibogaine. Thus, by administering the compounds of the present invention and compositions containing the same, a prolonged anti-craving effect may be obtained in mammals.

Generally, the present invention provides compounds of the formula:

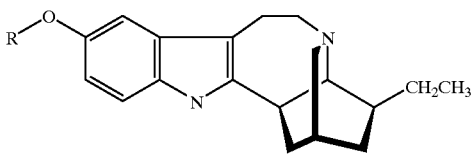

wherein R is hydrogen or a hydrolyzable group, such as hydrolyzable esters of from about 1 to 12 carbons. Such compounds may be administered either as single compounds, mixtures of compounds or as composition for reducing craving in mammals and/or treating chemical dependency.

Generally,. in the above formula, R is hydrogen or a group of the formula:

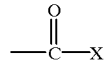

wherein X is a $C_1$–$C_{12}$ group, which is unsubstituted or substituted. For example, X may be a linear alkyl group such as methyl, ethyl, n-propyl, n-butyl, n-pentyl, n-hexyl, n-heptyl, n-octyl, n-nonyl, n -decyl, n-undecyl or n-dodecyl, or a branched alkyl group, such as i-propyl or sec-butyl. Also, X may be a phenyl group or benzyl group, either of which may be substituted with lower alkyl groups or lower alkoxy groups. Generally, the lower alkyl and/or alkoxy groups have from 1 to about 6 carbons. For example, the group R may be acetyl, propionyl or benzoyl. However, these groups are only exemplary.

Generally, for all groups X, they may either be unsubstituted or substituted with lower alkyl or lower alkoxy groups. For example, substituted X may be o-, m- or p-methyl or methoxy benzyl groups.

The compounds of the present invention specifically include all those of the formula (I) which in includes 12-hydroxy-ibogamine or those compounds which are hydrolyzed in vivo in mammals to form 12-hydroxy ibogamine. These compounds may be used singly or in admixture with one or more of such compounds.

Furthermore, the compounds of the present invention may be used either in the free base form or in the form of a pharmaceutically acceptable acid addition salt, such as, for example, the hydrochloride, hydrobromide, sulfate or phosphate salt.

The compounds of the present invention may be made in several ways. For example, 12-hydroxy ibogamine (noribogaine) may be synthesized by O-demethylation of ibogaine. This may be effected, for example, by reacting ibogaine with boron tribromide/methylene chloride at room temperature and isolating and purifying the product using known methodologies.

From noribogaine, any of the hydrolyzable esters of the present invention may be synthesized by reacting noribogaine with an appropriate anhydride or acyl chloride with or without a catalyst, such as pyridine. For example, 12-hydroxy ibogamine can be reacted with acetic anhydride in the presence of pyridine catalyst to yield 12-acetoxyibogamine. This specific example may be modified by using the appropriate anhydride or acyl chloride to form any of the present esters. The anhydrides and/or acyl chlorides so used are all either known compounds or can be synthesized from known compounds using known reactions.

See also *J. Org. Chem.*, vol. 59,8 (1994), Repke et al.

In accordance with the present invention, any single compound or mixture of compounds may be administered to a mammal in the amounts described in any one of U.S. Pat. Nos. 4,587,243; 4,857,523, 4,499,076, 5,026,697 or 5,152,994, each of which is incorporated herein in the entirety. Moreover, administration thereof may be from one to three times daily depending upon the need of the patient mammal to reduce craving for the substance of interest.

Generally, the present compounds or mixtures thereof are administered in an amount of from about 0.01 mg to about 100 mg per kg of body weight per day. The precise amount administered will vary as needed.

The present invention also provides pharmaceutical compositions for treating drug dependency in mammals. These compositions generally contain one or more of the compounds of the present invention in combination with a pharmaceutically acceptable carrier. Other excipients may also be added.

In accordance with the present invention, the compounds or compositions thereof may be administered in any manner, such as orally, intravenously, intramuscularly or interpertioneally. The present compositions may be compounded in any conventional manner using conventional excipients. For example, the present compositions may be compounded as capsules, tablets, pills, powders or solutions. Additionally, excipients, such as conventional binders and/or fillers, may be used.

Furthermore, the excipient and carrier formulations used for the present compositions may be those as described, for example, in U.S. Pat. Nos. 5,192,746 and 5,132,408. However, any conventional and pharmaceutically acceptable excipient may be used.

Generally, any means of formulating the present compounds or compositions may be used. For example, any suitable solid or liquid formulation may be used. Moreover, any conventional time-release formulation may be used with the compounds and solid compositions of the present invention.

Furthermore, the present compounds or compositions containing the same may be administered in any manner, such as, for example, orally, by suppository or by rectal infusion in the same manner as described in any of U.S. Pat. Nos. 4,587,243, 4,857,523, 4,499,096, 5,026,697 and 5,152,994.

In accordance with the present invention, the present invention may be used to treat chemical dependency in mammals for any substance which as the tendency to lead to such dependency. Such substances may be, but are not limited to, heroin, cocaine, PCP, marijuana, alcohol, nicotine, metamphetamine, opium, methadone, hycodan, morphine and caffeine. Generally, the present compounds are administered in an amount of about 0.01 mg to about 100 mg per kg of body weight per day. The compounds may be administered from one to up to several times per day, if necessary.

Of course, the chemical dependency treated in accordance with the present invention is not limited to heroin, cocaine, PCP, marijuana, alcohol, nicotine and caffeine. Rather, any type of chemical dependency may be treated thereby. As used herein, the term "chemical dependency" is intended to mean dependency of a mammal upon any single chemical, mixtures of chemicals, natural or synthetic product or mixture of all of the above which tend to promote repeated self-administration thereof. The mammals treated herein may be humans, cats, dogs, livestock or laboratory animals, such as rats, mice or rabbits, for example.

Furthermore, although the present invention is generally used in conjunction with humans, any mammals, such as dogs, cats, livestock or poultry may be treated as needed with adjustments being made for differences in body weight.

Quite surprisingly, in accordance with the present invention, it has been discovered that the present compounds, when administered, have a much longer lasting effect in reducing chemically dependent cravings in the mammalian body than ibogaine.

Furthermore, in accordance with the present invention, the long plasma half-life of the present compounds has been correlated with the long duration of psychoactive effects in mammals. Generally, the plasma half-life of the present compounds in mammals is from about 2 to 8 hours. However, the present compounds have been detected in human plasma and urine samples at four weeks post administration.

Finally, it is noted that for the sake of convenience, the compounds of the present invention may also be referred to as "noribogaine" or derivatives thereof.

In order to more fully describe the present invention, reference will now be made to certain examples which are provided solely for illustration and are not intended to be limitative.

EXAMPLE

An amount of ibogaine was administered to a human patient, and the plasma concentration of both ibogaine and a metabolite thereof, 12-hydroxy ibogamine, were observed as a function of time.

FIG. 1 illustrates the result of administering a certain dosage of ibogaine to a human patient, where the plasma concentration of ibogaine is measured over time. In essence, a peak plasma concentration of about 1,100 ng/ml is observed at administration. It is also notable that at about 11 hours after ibogaine administration, plasma concentration of ibogaine diminished to less than 400 ng/ml. After about 24 hours, plasma concentration diminished to less than 200 ng/ml. Thus, ibogaine is rather quickly eliminated by the patient.

Figure 2:
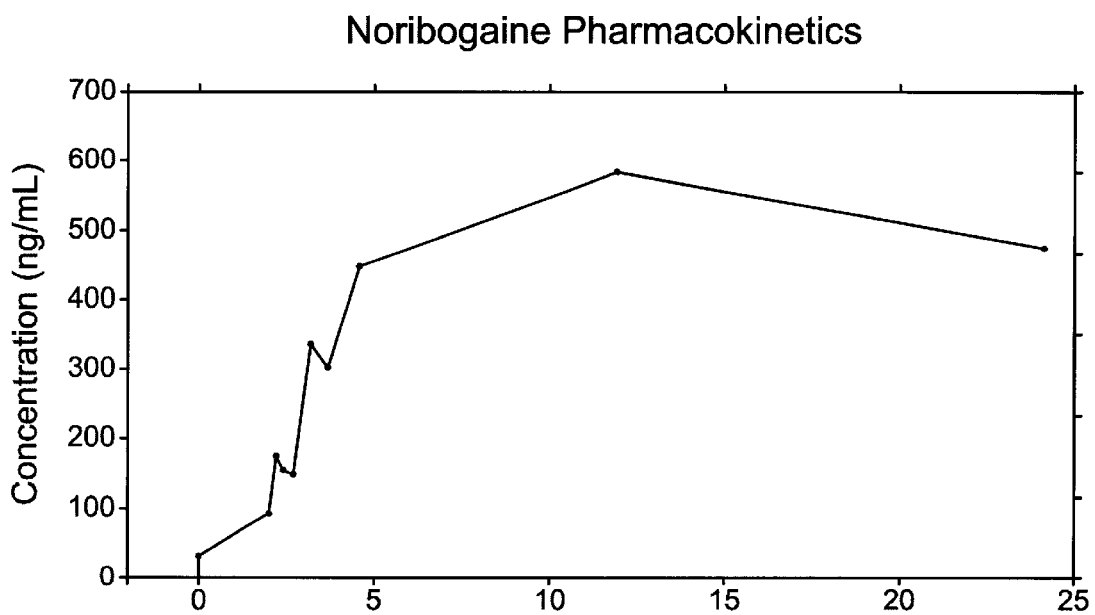
FIG. 2 is a graphical plot of noribogaine (12-hydroxy ibogamine) pharmacokinetics in a human as a function of blood concentration versus time.

By contrast, FIG. 2 illustrates the variation of noribogaine plasma concentration with time as a metabolite from the same ibogaine administration described above. In essence, a peak plasma concentration of noribogaine of about 590 ng/ml was reached only after about 11 hours from administration. Thereafter, even at 24 hours, a plasma concentration of greater than 500 ng/ml was observed. Thus, noribogaine exhibits a much longer plasma half-life than ibogaine and, thus, is much longer lasting in effect.

The present invention may also be advantageously used with laboratory animals in assessing the addictive potential in humans of present and prospective future addictive agents. As such, conventional methods of testing may be used in conjunction with the compounds and compositions of the present invention.

Clearly, numerous modifications and variations of the present invention are possible in light of the above teachings. It is, therefore, to be understood that within the scope of the appended claims, the invention may be practiced otherwise than as specifically described herein.

What is claimed as new and desired to be secured by Letters Patent of the United States is:

1. An essentially pure noribogaine compound having the formula:

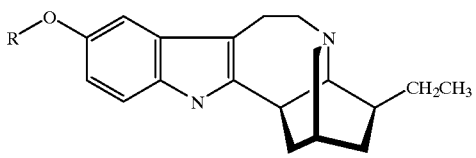

wherein R is hydrogen or a hydrolyzable group of the formula:

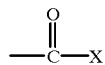

wherein X is an unsubstituted $C_1$–$C_{12}$ alkyl, alicyclic, aryl, saturated/unsaturated structures or a $C_1$–$C_{12}$ group substituted by lower alkyl or lower alkoxy groups, wherein said noribogaine compound having said hydrolyzable group hydrolyses in vivo to form 12-hydroxy ibogamine.

2. The noribogaine compound of claim 1, wherein X is $C_1$–$C_6$ group.

3. The noribogaine compound of claim 2, wherein X is methyl or ethyl.

4. The noribogaine compound of claim 1, wherein R is benzoyl.

5. The noribogaine compound of claim 1, wherein R is hydrogen.

6. A pharmaceutical composition for treating chemical dependency in a mammal, which comprises:

a) an amount of one or more noribogaine compounds having the formula:

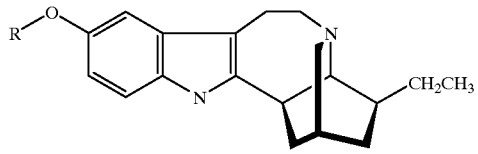

wherein R is hydrogen or a hydrolyzable alkyl, alicyclic, aryl, saturated/unsaturated structures of the formula:

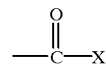

wherein X is an unsubstituted $C_1$–$C_{12}$ group or a $C_1$–$C_{12}$ group substituted by lower alkyl or lower alkoxy groups, effective to reduce craving for a chemical substance in said mammal, thereby treating the chemical dependency, and b) a pharmaceutically acceptable excipient.

7. The pharmaceutical composition of claim 6, wherein in said noribogaine compound, X is $C_1$–$C_6$ group.

8. The pharmaceutical composition of claim 7, wherein X is methyl or ethyl.

9. The pharmaceutical composition of claim 6, wherein R is benzoyl.

10. The pharmaceutical composition of claim 6, wherein said R is hydrogen.

11. A method of treating chemical dependency in a mammal, which comprises administering to said mammal an amount of the noribogaine compound of claim 1 or the pharmaceutical composition of claim 6 effective to treat said chemical dependency.

12. The method of claim 11, wherein said mammal is human.

13. The method of claim 11, wherein said chemical dependency is to a substance selected from the group consisting of heroin, cocaine, alcohol, nicotine, amphetamine, methamphetamine, opium, methadone, hycodan, morphine and caffeine.

14. The method of claim 11, wherein said noribogaine compound is 12-hydroxy ibogamine.

15. A method of treating addiction to a drug in a mammal in need thereof, which comprises administering to said mammal an amount of the noribogaine compound of claim 1 or the pharmaceutical composition of claim 6 effective to reduce craving or withdrawal symptoms or both for aid drug.

16. The method of claim 15, wherein said mammal is human.

17. The method of claim 15, wherein said drug is selected from the group consisting of heroin, cocaine, methamphetamine, opium, methadone, hycodan, morphine, amphetamine, alcohol, caffeine and nicotine.

18. The method of claim 15, wherein withdrawal symptoms from the drug are reduced.

* * * * *

(12) EX PARTE REEXAMINATION CERTIFICATE (8923rd)
United States Patent
Mash et al.

(10) Number: US 6,348,456 C1
(45) Certificate Issued: Mar. 27, 2012

(54) METHOD OF TREATING CHEMICAL DEPENDENCY IN MAMMALS AND A COMPOSITION THEREFOR

(75) Inventors: Deborah C. Mash, Miami, FL (US); Juan Sanchez-Ramos, Miami, FL (US); W. Lee Hearn, Miami, FL (US)

(73) Assignee: Demerx, Inc., Destin, CA (US)

Reexamination Request:
No. 90/011,498, Mar. 29, 2011

Reexamination Certificate for:
Patent No.: 6,348,456
Issued: Feb. 19, 2002
Appl. No.: 08/727,123
Filed: Oct. 8, 1996

(51) Int. Cl.
*A61K 31/55* (2006.01)
*C07D 487/22* (2006.01)
*C07D 487/00* (2006.01)

(52) U.S. Cl. .................. 514/214.03; 514/216; 540/520; 540/521

(58) Field of Classification Search .................. None
See application file for complete search history.

(56) References Cited
PUBLICATIONS

To view the complete listing of prior art documents cited during the proceeding for Reexamination Control Number 90/011,498, please refer to the USPTO's public Patent Application Information Retrieval (PAIR) system under the Display References tab.

*Primary Examiner* — Evelyn Huang

(57) ABSTRACT

An essentially pure noribogaine compound having the formula:

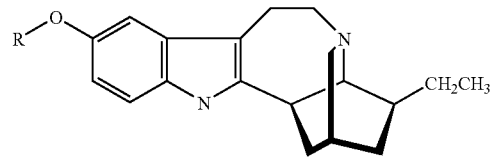

wherein R is hydrogen or a hydrolyzable group of the formula:

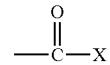

wherein X is an unsubstituted $C_1$-$C_{12}$ group or a $C_1$-$C_{12}$ group substituted by lower alkyl or lower alkoxy groups, wherein the noribogaine compound having the hydrolyzable group hydrolyzes in vivo to form 12-hydroxy ibogamine.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-10 and 14 are cancelled.

Claims 11 and 15 are determined to be patentable as amended.

Claims 12, 13 and 16-18, dependent on an amended claim, are determined to be patentable.

New claims 19-25 are added and determined to be patentable.

11. A method of treating chemical dependency in a mammal, which comprises administering to said mammal an amount of [the noribogaine compound of claim 1 or the] *a* pharmaceutical composition [of claim 6] effective to treat said chemical dependency, *wherein said pharmaceutical composition comprises:*

*(a) an amount of the compound of the formula:*

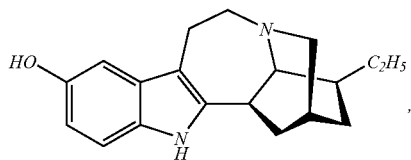

*wherein said amount is effective to reduce craving for a chemical substance in said mammal, thereby treating the chemical dependency, and*

*(b) a pharmaceutically acceptable excipient.*

15. A method of treating addiction to a drug in a mammal in need thereof, which comprises administering to said mammal [an amount of the noribogaine compound of claim 1 or the] *a* pharmaceutical composition comprising [of claim 6 effective to reduce craving or withdrawal symptoms or both for aid drug]

*(a) an amount of a compound of the formula:*

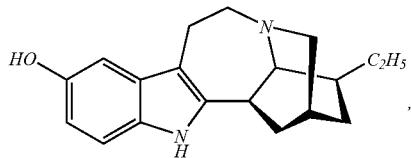

*wherein said amount is effective to reduce craving or withdrawal symptoms or both for the drug in said mammal, thereby treating the addiction to the drug, and*

*(b) a pharmaceutically acceptable excipient.*

*19. A method of treating chemical dependency in a mammal, which comprises administering to said mammal an amount of a pharmaceutical composition effective to treat said chemical dependency, wherein said pharmaceutical composition comprises*

*(a) an amount of one or more compounds of the formula:*

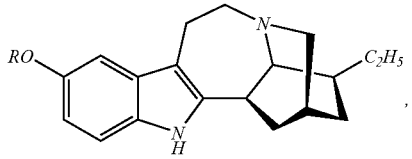

*wherein R is a hydrolyzable alkyl, alicyclic, aryl, saturated/unsaturated structure of the formula:*

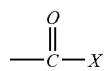

*wherein X is an unsubstituted $C_1$-$C_{12}$ group or a $C_1$-$C_{12}$ group substituted by lower alkyl or lower alkoxy groups, wherein said amount is effective to reduce craving for a chemical substance in said mammal, thereby treating the chemical dependency, and*

*(b) a pharmaceutically acceptable excipient.*

*20. The method of claim 19, wherein said mammal is human.*

*21. The method of claim 19, wherein said chemical dependency is to a substance selected from the group consisting of heroin, cocaine, alcohol, nicotine, amphetamine, methamphetamine, opium, methodone, hycodan, morphine and caffeine.*

*22. A method of treating addiction to a drug in a mammal in need thereof, which comprises administering to said mammal a pharmaceutical composition comprising*

*(a) an amount of one or more compounds of the formula:*

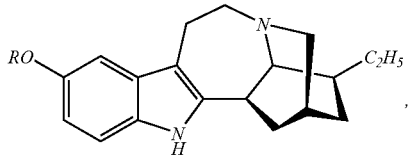

*wherein R is a hydrolyzable alkyl, alicyclic, aryl, saturated/unsaturated structure of the formula:*

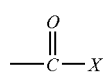

*wherein X is an unsubstituted $C_1$-$C_{12}$ group or a $C_1$-$C_{12}$ group substituted with lower alkyl or lower alkoxy groups, wherein said amount is effective to reduce craving or withdrawal symptoms or both for the drug in said mammal, thereby treating the addiction to the drug, and*

*(b) a pharmaceutically acceptable excipient.*

*23. The method of claim 22, wherein said mammal is human.*

*24. The method of claim 22, wherein said drug is selected from the group consisting of heroin, cocaine, methamphetamine, opium, methadone, hycodan, morphine, amphetamine, alcohol, caffeine and nicotine.*

*25. The method of claim 22, wherein withdrawal symptoms from the drug are reduced.*

* * * * *